United States Patent [19]

Wambach et al.

[11] Patent Number: 4,874,865

[45] Date of Patent: Oct. 17, 1989

[54] PREPARATION OF SUBSTITUTED LACTAMS

[75] Inventors: Ludwig Wambach, Heidelberg; Martin Fischer, Ludwigshafen, both of Fed. Rep. of Germany

[73] Assignee: BASF Aktiengesellschaft, Ludwigshafen, Fed. Rep. of Germany

[21] Appl. No.: 200,956

[22] Filed: Jun. 2, 1988

[51] Int. Cl.$^4$ .................. C07D 211/76; C07D 207/26
[52] U.S. Cl. ..................................... 546/243; 548/551
[58] Field of Search ....................... 546/243; 548/551

[56] References Cited

U.S. PATENT DOCUMENTS

| | | | |
|---|---|---|---|
| 3,332,938 | 7/1967 | Mayhew et al. | 540/485 |
| 3,959,356 | 5/1976 | Metcalf et al. | 560/172 |
| 4,235,778 | 11/1980 | Gittos et al. | 548/531 |

FOREIGN PATENT DOCUMENTS

| | | | |
|---|---|---|---|
| 0144664 | 6/1985 | European Pat. Off. | |
| 51-4166 | 1/1976 | Japan | 548/551 |
| 52-48658 | 4/1977 | Japan | 548/551 |

OTHER PUBLICATIONS

March, J., *Advanced Organic Chemistry*, McGraw Hill, New York, 1968, pp. 309, 753–754, 756 and 757.
G. I. Nikishin et al., *Bulletin of the Academy of Sciences, USSR, Div. of Chem. Science*, 1964, pp. 1745–1748.

*Primary Examiner*—Richard A. Schwartz
*Attorney, Agent, or Firm*—Keil & Weinkauf

[57] ABSTRACT

Preparation of substituted lactams Ia to Ic

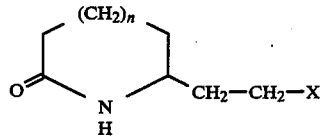

Ia

-continued

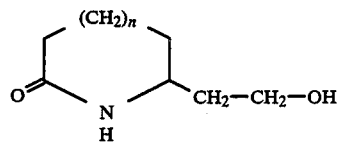

Ib

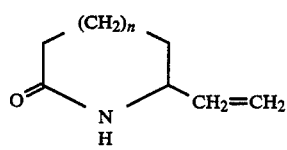

Ic where n is 0 or 1, X is $-O-CO-R^1$, $-O-SO_2-R^1$, $-CO-R^2$, $-CO-O-R^3$ or $-CO-NR^4R^5$, $R^1$ is a $C_1$-$C_8$-radical of a carboxylic or sulfonic acid, $R^2$ is $C_1$-$C_8$-alkyl, $R^3$ is H or alkyl, aryl or aralkyl of not more than 8 carbon atoms, $R^4$ and $R^5$ are each H or $C_1$-$C_4$-alkyl or together form a 5-membered or 6-membered ring, by reacting a lactam II

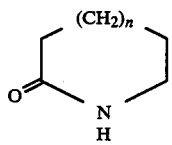

II with a vinyl compound III

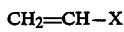

and a compound IV which forms free radicals to give Ia, and preparation of Ib by hydrolysis of a compound Ia in which X is $(-O-CO-R^1)$ or $(-O-SO_2-R^1)$, and preparation of Ic by thermolysis of Ib or of a compound Ia in which X is $(-O-CO-R^1)$ or $(-O-SO_2-R^1)$, and the novel substituted lactams Ia and Ib where X is $(-O-CO-R^1)$ and $(-O-SO_2-R^1)$.

3 Claims, No Drawings

PREPARATION OF SUBSTITUTED LACTAMS

The present invention relates to a novel process for the preparation of substituted lactams of the general formulae Ia to Ic

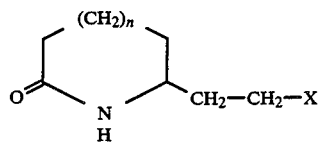

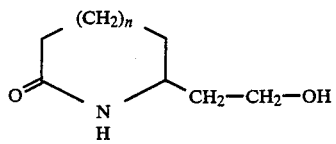

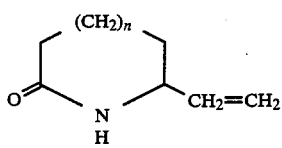

where n is 0 or 1 and X is one of the following groups
—O—CO—$R^1$
—O—SO$_2$—$R^1$
—CO—$R^2$
—CO—O—$R^3$
—CO—NR$^4$R$^5$ where $R^1$ is a radical of a carboxylic or sulfonic acid of 1 or 8 carbon atoms, $R^2$ is $C_1$-$C_8$-alkyl, $R^3$ is hydrogen or an alkyl, aryl or aralkyl group of not more than 8 carbon atoms and $R^4$ and $R^5$ are each hydrogen or $C_1$-$C_4$-alkyl and may furthermore be bonded to form a 5-membered or 6-membered ring.

The present invention furthermore relates to novel substituted lactams Ib and to lactams Ia in which the radical X is a (—O—CO—$R^1$) or (—O—SO$_2$—$R^1$) group.

U.S. Pat. No. 3 332 938 discloses that lactams II'

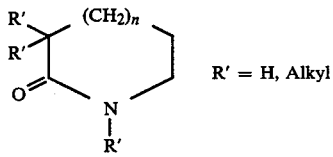

where R' is H or alkyl, and α-olefins R"-CH$_2$=CH$_2$ can be reacted with the aid of compounds, such as organic peroxides, which form free radicals to give substituted lactams I'

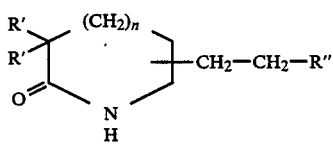

but mixtures of different substitution products are obtained. For example, the reaction of pyrrolid-2-one with oct-1-ene gives about 25–30% of 3-octylpyrrolid-2-one and 60–65% of 5-octylpyrrolid-2-one. Similar observations are reported by G. I. Nikishin and R. I. Mustafaer in their article entitled Free radical addition of 2-pyrrolidone to α-olefins (Bulletin of the Academy of Sciences, USSR, Div. of Chem. Science, 1964, pages 1745–1748).

Furthermore, EP-A-O 144 664 discloses vinyllactams Ic

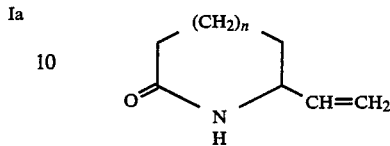

which are obtainable by the process described there but only in an extremely involved manner via the corresponding ω-cyanomethyllactams.

Since the ring cleavage of Ic leads to a group of important drugs, including the transaminase inhibitor Ic' (described in more detail in U.S. Pat. No. 4 235 778 and 3 959 356),

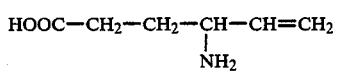

it is a specific object of the present invention to make the vinyllactams Ic more readily obtainable.

It is a general object of the present invention to provide an economical and universally applicable process for the selective introduction of the radicals CH$_2$—CH$_2$—X and —CH$_2$—CH$_2$—OH into the ω-position of lactams II

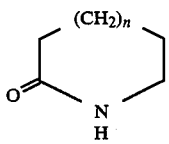

and the novel intermediates obtainable by the said process and lactams Ia in which X is a (—O—CO—$R^1$) or (—O—SO$_2$—$R^1$) group.

We have found that these objects are achieved by a process for the preparation of substituted lactams of the general formulae Ia to Ic

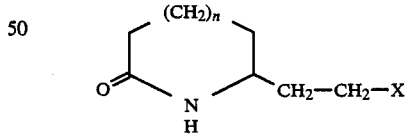

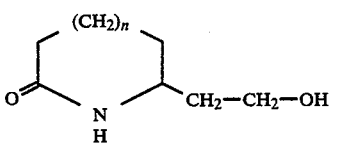

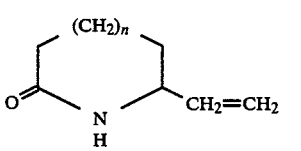

where n is 0 or 1 and X is one of the following groups
—O—CO—$R^1$
—O—$SO_2$—$R^1$
—CO—$R^2$
—CO—O—$R^3$
—CO—$NR^4R^5$ where $R^1$ is a radical of a carboxylic or sulfonic acid of 1 to 8 carbon atoms, $R^2$ is $C_1$-$C_8$-alkyl, $R^3$ is hydrogen or an alkyl, aryl or aralkyl group of not more than 8 carbon atoms and $R^4$ and $R^5$ are each hydrogen or $C_1$-$C_4$-alkyl and may furthermore be bonded to form a 5-membered or 6-membered ring, wherein (a) for the preparation of Ia, a lactam of the general formula II

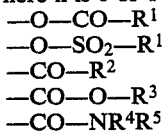

II is reacted at from 100° to 200° C. with a vinyl compound of the general formula III $CH_2=CH-X$    III and a compound IV which forms free radicals, (b) for the preparation of Ib, a compound Ia in which X is a (—O—CO—$R^1$) or (—O—$SO_2$—$R^1$) group is subjected to hydrolytic cleavage, and (c) for the preparation of Ic from a compound Ib or from a compound Ia in which X is a (—O—CO—$R^1$) or (O—$SO_2$—$R^1$) group, water or an acid $R^1$—COOH or $R^1$—$SO_3H$ is eliminated by heating.

Among the starting compounds II, pyrrolid-2-one and the piperidin-2-one, the pyrrolid-2-one is particularly important with regard to the preparation of the physiologically important γ-amino acid Ic'. An important advantage of the novel process lies in the fact that these starting materials are cheap commercial compounds.

Examples of vinyl compounds III are:

aliphatic vinyl carboxylates, in particular those of $C_2$-$C_4$-fatty acids, including in particular vinyl acetate and vinyl propionate; $R^1$ may furthermore be an aromatic, araliphatic or cycloaliphatic radical which may carry inert substituents, such as halogen;

vinyl sulfonates, in particular vinyl toluenesulfonate; in general, the same applies to radical $R^1$ as for the vinyl carboxylates;

vinyl ketones, such as vinyl methyl ketone and vinyl propyl ketone;

acrylic acid and acrylates, such as methyl acrylate, ethyl acrylate, phenyl acrylate and benzyl acrylate, and acrylamides, such as the parent compounds of this class of compounds, N,N-dimethylacrylamide and N-acryloylpiperidine.

If it is intended to prepare the compounds Ib, a particularly preferred vinyl compound III for economic and process engineering reasons is vinyl acetate while the compounds Ib which act as intermediates in this case and the reaction products of the lactams II with vinyl acetate and vinyl toluenesulfonate are particularly suitable for the preparation of Ic.

Suitable free radical formers IV for process step (a) are all peroxides and azo compounds which are used for free radical polymerization of olefinically unsaturated monomers, for example hydroperoxides, such as tert-butyl hydroperoxide and cumene hydroperoxide, dialkyl peroxides, such as di-tert-butyl peroxide, diacyl peroxides, such as dibenzoyl peroxide, peroxy acids and their esters, such as perbenzoic acid and tert-butyl perbenzoate, and azo compounds, such as azobisisobutyronitrile. Di-tert-butyl peroxide is particularly preferred. Otherwise, the choice of the free radical formers depends on the reaction temperature, in that it is advantageous to use a free radical former whose decomposition temperature is slightly below the reaction temperature.

The amount of the free radical former is in general from 5 to 20, preferably from 8 to 15, mol %, based on the vinyl compound III. Below 5 mol %, the reaction slows down excessively, while amounts larger than 30 mol % have no economic advantages.

The range of 100°-200° C. for the reaction temperature is based on the fact that, on the one hand, a larger number of free radical chain fragments are expected at below 100° C. and, on the other hand, side reactions are observed at above 200° C. As a rule, the reaction is preferably carried out at from 130° to 180° C.

In principle, the pressure has no effect on the reaction, so that it is preferably carried out under atmospheric pressure; however, a higher pressure, for example up to 10 bar, may be advisable if the vinyl compound III, for example vinyl acetate, is volatile under the reaction conditions.

In order as far as possible to suppress the polymerization of the vinyl compounds III, which is always in competition with the reaction according to the invention, it is advantageous to ensure that the lactam II is always present in a large excess during the reaction, for example by initially taking it together with the free radical former and gradually adding the vinyl compound at the reaction temperature. In another possible method, the vinyl compound and a solution of the free radical former in II are combined synchronously, if necessary in initially taken II. It is advisable to use II and III in a molar ratio of from 2:1 to 50:1, preferably from 5:1 to 20:1, based on the total reaction (a).

Solvents need not in principle be present since the lactams II are generally used in excess and simultaneously serve as solvents and diluents. If it is nevertheless intended to use solvents, for example in order to use the vinyl compounds III or the free radical formers IV in the form of solutions other than those in the Lactams II, suitable solvents for this purpose are, for example, chlorobenzene and the dichlorobenzenes, in amounts of not more than 500% by volume, based on the component to be dissolved.

It is frequently advantageous to carry out the reaction under an inert gas atmosphere in order to prevent reactions with atmospheric oxygen, which are promoted by the free radical former.

The reaction mixtures can be worked up in a conventional manner to obtain the products Ia, for example by destroying the excess free radical former with a reducing agent, such as an iron(II) salt or an iodide solution, then distilling off the major part of the lactam II and, where relevant, the solvent, and allowing Ia to crystallize out from the residue, if necessary after the addition of a solubility-reducing solvent. In many cases, however, Ia can be isolated by distillation alone.

The reaction times required for the preparation of Ia are in general from 1 to 5 hours. The compounds Ia are obtained as a rule in yields of from 50 to 85%, based on the vinyl compound III. It is noteworthy that the proportion of isomeric compounds is generally negligibly small.

In process step (b), for the preparation of the compounds Ib, compounds Ia in which X is a (—O—CO—$R^1$) or (—O—$SO_2$—$R^1$) group are used as starting materials, the reaction mixtures of process step (a) advantageously being used since it is generally not necessary to purify Ia.

The hydrolytic cleavage is advantageously carried out using an excess of water and in the presence of a catalytic amount of a mineral acid, such as sulfuric acid, or using an acidic ion exchanger or with a stoichiometric amount of a mineral base, such as sodium hydroxide solution or of a tertiary amine, such as triethylamine, at about 50°–120° C., in a conventional manner. In another possible method, an excess of acid is used and the reaction mixture is then neutralized again. The alcohol Ib can be isolated in a conventional manner, so that further discussion in this respect is unnecessary. The ω-hydroxyethyllactams Ib are obtained in virtually quantitative yield.

In process step (c), to obtain the compounds Ic, the water is eliminated from the compounds Ib or the acid $R^1$—COOH or $R^1$—$SO_2$—OH is eliminated from the corresponding compounds Ia by heating in the presence or absence of a catalyst; in this procedure, the starting materials are evaporated and the residue is heated to 300°–700° C. In the dehydradation of Ib, it is preferable to use known dehydradation catalysts, such as alumina or a zeolite, as catalysts.

The cleavage products are condensed and the condensate is worked up in a conventional manner, preferably by distillation, to obtain the ω-vinyllactams Ic. The yields of Ic are as a rule from 80 to 95%, based on Ia or Ib used.

The novel process makes it possible to obtain virtually isomer-free ω-substituted lactams from cheap starting materials in a simple manner, the said lactams being useful intermediates for organic synthesis and for the preparation of physiologically active substances, including the transaminase inhibitors Ic'.

EXAMPLE 1

5-(2-acetoxy)-ethylpyrrolid-2-one (Ia/1)

A mixture of 255 g (3 moles) of pyrrolid-2-one, 258 g (3 moles) of vinyl acetate and 88 g (0.6 mole) of di-tert-butyl peroxide was added gradually, in the course of 9 hours and under a nitrogen atmosphere, to 2550 g (30 moles) of pyrrolid-2-one which was kept at 150° C. After a further 2 hours at 150° C., the reaction mixture was worked up by distillation to obtain the product Ia/1; bp.: 143°–146° C./0.15 mbar; yield 60%.

EXAMPLE 2

5-(2-methoxycarbonyl)-ethylpyrrolid-2-one (Ia/2)

This compound was prepared similarly to Example 1 from pyrrolid-2-one and methyl acrylate. Yield 80%; bp.: 135°–138° C./0.15 mbar; mp.: 60°–62° C.

EXAMPLE 3

6-(2-acetoxy)-ethylpiperid-2-one (Ia/3)

This compound was prepared similarly to Example 1 from pyrrolid-2-one and vinyl acetate. Yield 55%; bp.: 140°–143° C./0.1 mbar.

EXAMPLE 4

6-(2-hydroxy)-ethylpiperid-2-one (Ib/1)

74 g (0.4 mole) of the piperidone Ia/3 described in Example 3 were heated with 500 ml of 20% strength by weight sulfuric acid for 8 hours, after which the reaction mixture was neutralized with sodium hydroxide solution and diethyl ether was then added as an extracting agent. The ether was stripped off from the dry ether phase, and the residue was recrystallized from methyl acetate/cyclohexane. Yield of Ib/1 75%; mp.: 78°–80° C.

EXAMPLE 5

Preparation of 5-vinylpyrrolid-2-one (Ic/1)

A stream of 40 l/h of nitrogen which contained about 26 g/l of the pyrrolidone Ia/1 described in Example 1 was passed through a tube reactor which had a height of 45 cm and an internal diameter of 3 cm, was heated at 52° C. and was filled with porcelain rings of 5 mm diameter. The residence time of the gas in the reactor was about 28 sec. After passing through the reactor, the gas stream was cooled, and the composition of the condensate obtained showed that conversion of Ia/1 was 70%, the selectivity with respect to the vinylpyrrolidone Ic/1 being 85%. Bp.: 85°–90° C./0.1 mbar.

EXAMPLE 6

Preparation of 5-(2-carboxy)-ethylpyrrolid-2-one (Ia/4)

This compound was prepared similarly to Example 1 from pyrrolid-2-one and acrylic acid. Yield: 63%; mp.: 123°–125° C.

We claim:

1. A process for the preparation of a substituted lactam of the formula Ia, Ib or Ic

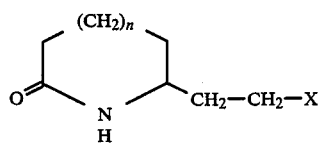

Ia

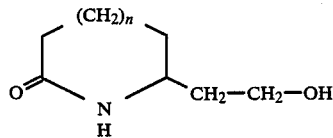

Ib

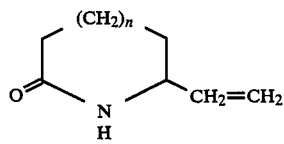

Ic where n is 0 or 1 and X is one of the following groups

—O—CO—$R^1$
—O—$SO_2$—$R^1$
—CO—$R^2$
—CO—O—$R^3$
—CO—$NR^4R^5$ where $R^1$ is a radical of a carboxylic or sulfonic acid of 1 to 8 carbon atoms, $R^2$ is $C_1$–$C_8$-alkyl, $R^3$ is hydrogen or an alkyl, aryl or aralkyl group of not more than 8 carbon atoms and $R^4$ and $R^5$ are each hydrogen or $C_1$-$C_4$-alkyl and may furthermore be bonded to form a 5-membered or 6-membered ring, wherein
(a) for the preparation of Ia, a lactam of the formula II

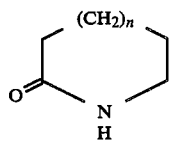

is reacted at from 100° to 200° C. with a vinyl compound of the formula III $CH_2=CH-X$  III and a compound IV which forms free radicals,
(b) for the preparation of Ib, a compound Ia prepared as in part a above in which X is a (—O—CO—$R^1$) or (—O—SO$_2$—$R^1$) group is subjected to hydrolytic cleavage, and
(c) for the preparation of Ic from a compound Ib prepared as in part b above or from a compound Ia prepared as in part a above in which X is a (—O—CO—$R^1$) or (—O—SO$_2$—$R^1$) group, water or an acid $R^1$—COOH or $R^1$—SO$_3$H is eliminated by heating in the presence or absence of a catalyst.

2. A substituted lactam of the formula Ia

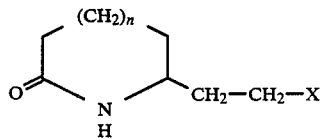

wherein X is a (—O—CO—$R^1$) or (O—SO$_2$—$R^1$) group, $R^1$ is a radical of a carboxylic or sulfonic acid of 1 to 8 carbon atoms and n is 0 or 1.

3. A substituted lactam of the formula Ib

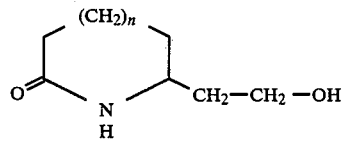

wherein n is 1.

* * * * *

UNITED STATES PATENT AND TRADEMARK OFFICE
CERTIFICATE OF CORRECTION

PATENT NO. : 4,874,865

DATED : October 17, 1989

INVENTOR(S) : Ludwig WAMBACH et al.

It is certified that error appears in the above-identified patent and that said Letters Patent is hereby corrected as shown below:

On the Cover Sheet

Please insert -- [30]  Foreign Application Priority Data
                June 3, 1987 [DE] Fed. Rep. of Germany ...3718563

Signed and Sealed this

Eleventh Day of June, 1991

Attest:

HARRY F. MANBECK, JR.

Attesting Officer

Commissioner of Patents and Trademarks